United States Patent [19]

Narayan et al.

[11] 4,054,546

[45] Oct. 18, 1977

[54] TRIAZINE COMPOSITIONS AND THEIR USE AS CATALYSTS

[75] Inventors: Thirumurti L. Narayan, Riverview; Moses Cenker, Trenton, both of Mich.

[73] Assignee: BASF Wyandotte Corporation, Wyandotte, Mich.

[21] Appl. No.: 677,902

[22] Filed: Apr. 19, 1976

Related U.S. Application Data

[62] Division of Ser. No. 534,436, Dec. 19, 1974, Pat. No. 3,988,337.

[51] Int. Cl.$^2$ .................. C08G 18/20; C08G 18/14
[52] U.S. Cl. .................. 260/2.5 BF; 260/2.5 AC; 260/2.5 AW; 260/75 NC; 260/77.5 AC
[58] Field of Search .................. 260/2.5 BF, 2.5 AC, 260/2.5 AW, 77.5 AC, 75 NC

[56] References Cited

U.S. PATENT DOCUMENTS

| 3,891,578 | 6/1975 | Kan | 260/2.5 BF |
|---|---|---|---|
| B 537,102 | 1/1976 | Cenker | 260/2.5 BF |

*Primary Examiner*—C. Warren Ivy
*Attorney, Agent, or Firm*—Bernhard R. Swick; Arnold S. Weintraub; Robert E. Dunn

[57] ABSTRACT

New triazine compositions having incorporated therewithin both alkanolamino groups and pendent tertiary amino groups are defined herein. The triazines are prepared by the reaction of (1) an intermediate prepared from either alkyl chlorides or alkylene oxides and dialkylaminoalkyl primary amines and (2) cyanuric chloride or a derivative thereof. The triazines hereof exhibit excellent catalytic activity in the preparation of rigid cellular foams characterized by carbodiimide linkages.

7 Claims, No Drawings

TRIAZINE COMPOSITIONS AND THEIR USE AS CATALYSTS

This is a divisional application of copending U.S. Pat. Application Ser. No. 534,436, filed Dec. 19, 1974 now U.S. Pat. No. 3,988,337.

BACKGROUND OF THE INVENTION

1. Field of the Invention

The present invention relates to triazine compositions, methods of preparation therefor and uses thereof. More particularly, the present invention pertains to triazine compositions having incorporated therewithin alkanolamino groups and pendent tertiary amino groups, methods of preparation therefor and uses thereof. Even more particularly, the present invention pertains to the preparation of triazines containing both alkanolamino and tertiary amino groups from intermediate secondary amines and the use of such triazines as catalysts for the preparation of cellular products.

2. Prior Art

There has been disclosed heretofore the use of triazine compounds as catalysts for the preparation of rigid cellular products characterized by carbdiimide linkages. The prior art has taught, inter alia, the use of both symmetrical and unsymmetrical triazines in the preparation of such cellular products. See, inter alia, U.S. Pat. Nos. 3,645,923 and 3,806,475.

Although these prior catalysts are extremely efficacious in their intended use, it has, generally, been found that it was essential to incorporate isocyanate trimerization catalysts therewith, to generate an exothermic reaction at room temperature. The exothermic reaction, in turn, activated the triazine catalyst. Thus, in essence, the reactivity of the of the prior art catalysts could be improved upon, i.e., exhibit a greater catalytic activity in the preparation of such cellular products.

To this end, it would be most beneficial to provide catalysts which possess the features of both carbodimide catalysts, i.e., alkanolamino triazines, and isocyanurate catalysts, i.e., hexahydrotriazine. It is to this with which the present invention is concerned.

SUMMARY OF THE INVENTION

In accordance with the present invention there is provided new triazine compositions which incorporate therewithin strongly basic pendent tertiary amino groups and alkanolamino groups. The triazines hereof are prepared from the reaction of (1) cyanuric chloride or a derivative thereof and (2) the reaction product of (a) a dialkylaminoalkyl primary amine with (b) either an alkylene oxide or an alkyl halide.

The triazines hereof are useful as catalysts for the preparation of rigid cellular products characterized by carbodiimide linkages. These products are generally prepared by the catalytic condensation of an organic polyisocyanate in the presence of a catalytically sufficient amount of the present triazines.

The triazines hereof, which are more reactive than heretofore known triazines, are enhanced by the conjoint use of an alkanol therewith.

For a more complete understanding of the present invention reference is made to the following detailed description and accompanying drawings.

DESCRIPTION OF THE PREFERRED EMBODIMENTS

The present invention, as hereinbefore noted, provides triazine compounds or compositions useful as catalysts for the preparation of rigid cellular products characterized by carbodiimide linkages. As will subsequently be explained in greater detail, the cellular products produced with the triazines hereof contain both carbodiimide and isocyanurate groups therewithin. However, for purposes of brevity these products shall be referred to as carbodiimide products.

The triazine compositions of the present invention may be represented by the following formula:

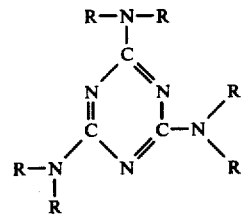

wherein R is either lower alkyl having from about one to six carbon atoms, 2-hydroxy lower alkyl having from about one to six carbon atoms, or $(R')_2N—R''$ wherein R' is lower alkyl having from about one to six carbon atoms and R'' is alkylene having from about one to ten carbon atoms and wherein at least one R must be 2-hydroxy lower alkyl and at least one R must be $(R')_2N—R''$, as defined above.

The triazines hereof are prepared by the reaction of cyanuric chloride or a derivative thereof with an intermediate derived from either an alkyl halide or alkylene oxide and a dialkylaminoalkyl primary amine. Generally, the reaction proceeds at a temperature of from about 0° to about 110° C for a period of from about one to six hours. The reaction is carried out in the presence of a base to neutralize liberated hydrochloric acid.

The cyanuric chloride is employed as a slurry or suspension thereof to which the intermediate is slowly added, at a temperature of from about −5° to about 35° C depending on the solvent. The base is then slowly added thereto. After the base addition is complete the reaction is allowed to proceed at the reaction temperatures hereinbefore noted.

Useful basses include, for example, sodium hydroxide, potassium hydroxide, lithium hydroxide, sodium carbonate, sodium bicarbonate, and the like. Also, tertiary alkylamines, such as tributylamine, as triethylamine, can be used herein as a base.

In carrying out the reaction the cyanuric chloride and intermediate are employed in a, respective, molar ratio of from about 1:1 to 1:3, depending upon the number of chlorines to be replaced, and, usually, 1:3.

The base is present in an amount equimolar to the intermediate.

The triazines hereof range from liquid compositions to viscous oils.

Representative of the compounds encompassed hereby are, for example, 2,4,6-tris[3-dimethylamino-N-(2-hydroxyethyl)propylamino]-s-triazine; 2,4-bis[bis(3-dimethylaminopropyl)amino]-6-(N-methyl-2-hydroxyethylamino)-s-triazine; 2,4-bis 6-[3-dimethylamino-N-(2-hydroxyethyl)propylamino]-s-triazine;

and 2,4-bis(N-methyl-2-diethylaminoethylamino)-6-(N-methyl-2-hydroxyethylamino)-s-triazine, and the like.

As noted, the triazines hereof are, generally, prepared by the reaction of cyanuric chloride or a derivative thereof with a new intermediate prepared from either an alkyl halide or an alkylene oxide and a dialkylaminoalkyl primary amine. The dialkylaminoalkyl primary amine used to prepare the intermediate, generally, corresponds to the formula:

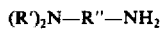

wherein R' and R'' are defined, as above.

The reaction of the primary amine with the alkyl halide or alkylene oxide proceeds in accordance with either of the following equations:

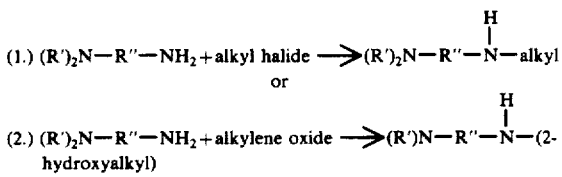

As is known to those skilled in the art, the first reaction, generally, takes place in the presence of a base, such as, sodium hydroxide, potassium hydroxide, lithium hydroxide, sodium bicarbonate, carbonate, potassium carbonate and the like. Preferably, where used, the basic compound is sodium hydroxide. The reaction generally proceeds at 50° to 125° C, preferably, 80° to 100° C.

With alkylene oxide addition, the reaction generally proceeds, under conventional oxyalkylation conditions, at a temperature ranging from about 20° to about 125° C, and usually, at about 60° C to about 90° C. Generally, the alkylene oxide and amine are reacted in a respective molar ratio ranging from abut 1:1 to about 1:10 and, preferably, from about 1:5 to about 1:10, and for a period of from about one to three hours.

Useful alkylene oxides include, for example, ethylene oxide, 1,2-propylene oxide, 1,2-butylene oxide, pentylene oxides, hexylene oxides, and the like. Generally, the alkylene oxides are those having from two to six carbon atoms in the alkylene portion thereof.

Useful alkyl halides include both substituted and unsubstituted, primary or secondary, and having from about one to six carbon atoms in the alkyl portin thereof. Useful, unsubstituted alkyl halides include, for example, methyl chloride, methyl idodide, ethyl chloride, ethyl bromide, n-propy chloride, i-propyl chloride, etc. Useful substituted alkyl halides include for example, 2-dimethylaminoethyl chloride, 2-diethylaminoethyl chloride, 3-dimethylaminopropyl chloride, 3-diethylaminopropyl chloride, 2-methyl-3-dimethylaminopropyl chloride or bromides or iodides.

In preparing the intermediate derived from the alkyl halide, the amine and akyl halide are reacted in a, respective, molar ratio of from about 20:1 to about 2:1, and, preferably, from about 15:1 to about 5:1. The reaction, generally, proceeds at a temperature ranging from about 50° to about 125° C and for a period of about one to ten hours. The times and temperatures will vary depending upon the reactants.

Preferably, the alkyl halide-based intermediate is prepared by adding the halide to the amine, after which the base is added thereto to neutralize any liberated acid in solution.

The secondary amine intermediates hereof are, generally, liquids which can be readily reacted with cyanuric chloride or a derivative thereof, such as, 2-chloro-4,6 bis(dibutylamino)-s-triazine, to provide the triazines hereof.

As hereinbefore noted the triazines hereof exhibit excellent catalytic activity in the preparation of rigid cellular products and, in particular, rigid cellular compositions characterized by carbodiimide linkages. These rigid cellular products, which are discussed in the hereinbefore referenced patents are rigid cellular products or foams which have isocyanurate and some free isocyanate groups therewithin, as well as, substantial amounts of carbodiimide linkages. Thus, the products are characteristically referred to as carbodiimide products or foams.

The foams hereof are generally prepared by the catalytic condensation of an organic polyisocyanate in the presence of a catalytically sufficient amount of the herein defined triazines. Generally, from about one-half part to about ten parts, by weight, of triazine per one hundred parts by weight of polyisocyanate is employed, and, preferably, from about one to five parts, by weight, of triazine per one hundred parts by weight of polyisocyanate.

It has also been found that by utilizing the triazines hereof conjointly with an alkanol that the catalytic activity of the triazine is enhanced. This was completely unexpected in that triazine catalytic activity enhancement with alkanols was unknown, heretofore, although isocyanurate catalysts have been known to be so-enhanced. See, inter alia, British Pat. No 824,420.

The alkanol can be used conjointly with the triazine in an amount ranging from about 0.25 to two parts by weight thereof per part by weight of triazine. Preferably, from about 0.5 to 1.5 parts of alkanol, by weight, per part of triazine is employed.

Useful alkanols include, for example, methanol, ethanol, n-propanol, i-propanol, n-butanol, i-butanol, t-butanol and the like, as well as mixtures thereof.

Any organic polyisocyanate can be efficaciously employed herein. Representative of the useful organic polyisocyanates include those enumerated in the hereinbefore referenced patents, as well as in U.S. Pat. Nos. 3,804,782; 3,732,187; and 3,717,596, etc., the disclosures of which are hereby incorporated by reference.

In preparing the rigid cellular products hereof the triazine or triazine and alkanol admixture can be used, alone, or in admixture with an isocyanurate or isocyanate trimerization catalyst. Useful isocyanate trimerization catalysts include those disclosed in the prior art.

In preparing rigid cellular products in accordance herewith, additional ingredients, such as, surfactants, plasticizers, fillers, active hydrogen-containing compounds, and the like can be utilized.

The foams hereof, it should also be noted, can be prepared by any suitable technique including the one-shot process disclosed in the above-referred to patents, as well as the quasi-prepolymer and two-stage processes disclosed in copending U.S. Patent Application Serial No. 511,111 October 2, 1974 and entitled "Urethane-Modified Carbdiimide-Isocyanurate Foams Prepared From TDI-Rich Iscyanates". In this regard it must be noted that in employing the latter two processes, any organic polyisocyanate can be utilized herein, not just solely major amounts of distilled toluene diisocyanate.

Also, it has been found that the present triazines are useful in the preparation of carbodiimide-isocyanurate resins.

For a more complete understanding of the present invention reference is made to the following examples. In the examples, which are not to be construed as limitative of the invention, all parts are by weight absent indications to the contrary.

EXAMPLE I

This example illustrates the preparation of a secondary amine intermediate in accordance with the present invention.

Into a three-liter vessel equipped with a dry ice condenser, agitation means, heating means, thermometer and gas inlet was charged 1550 parts (15 moles) of 3-dimethylaminopropylamine. The charge was gradually heated to 80° C. Over a period of abut 1.7 hours, 88 parts (2 moles) of ethylene oxide was bubbled into the amine, while maintaining the temperature in the vessel at about 80° C.

After the ethylene oxide addition was completed, the temperature in the vessel was gradually raised to 137° C over a period of 1.5 hours to ensure complete reaction.

After the reaction was completed, the dry ice condenser was removed and replaced with a twelve-inch Vigreaux Column and a fraction cutter. Excess dimethylaminopropylamine was stripped until the temperature in the vessel reached 160° C.

The liquid residue in the vessel was, then, transferred to a 500 ml. distillation vessel and was distilled under reduced pressure to yield 187.9 parts (64%) of a product having a boiling point of 81°-84° C at 0.18 to 0.22 Torr and identified as 3-dimethylamino-N-(2-hydroxyethyl)-propylamine.

EXAMPLE II

This example illustrates the preparation of another secondary amine intermediate in accordance with the present invention.

Into a reaction vessel equipped with heating means, agitation means, a thermometer, reflux condenser and an addition funnel was charged 306 parts (3 moles) of 3-dimethylaminopropylamine. The amine was heated to 100° C While maintaining the temperature thereat and with stirring an aqueous solution of 131.3 parts (0.3 mole) of 3-dimethylaminopropylchloride hydrochloride, was added thereto through the addition funnel over a period of 1.5 hours.

After the addition was completed and with continuing agitation, the contents in the vessel were heated at the reflux temperature, 108° C, for 3 hours, and, then, allowed to cool to room temperature. A 50% aqueous solution of 72 parts (1.8 moles) of sodium hydroxide was, then, added dropwise thereto over a period of 0.5 hours.

After the sodium hydroxide addition was completed, the contents of the vessel was stripped of the dimethylaminopropylamine-water mixture by gradually heating the vessel until the temperature therewithin reached 107° C.

The residual liquid in the vessel was distilled under reduced pressure to yield 68.2 parts (41%) of a product having a boiling point of about 65°-69° C at 0.3 to 0.4 Torr and identified as bis(3-dimethylaminopropyl)amine.

The following examples illustrate the preparation of triazine compounds in accordance with the present invention.

EXAMPLE III

Into a reaction vessel equipped with a thermometer, addition funnel, agitation means, reflux condenser and a cooling bath was charged 200 parts of water. The water was cooled to 0° C, then, 18.5 parts (0.1 mole) of cyanuric chloride was added, portionwise, to the water, with stirring. While still maintaining the temperature at 0° C, and with stirring, 48.2 parts (0.33 mole) of 3-dimethylamino-N-(2-hydroxyethyl)propylamine was added to the aqueous sooution over a one hour period. After the addition was completed the cooling bath was removed and replaced with heating means. Then, 13.2 parts (0.33 mole) of sodium hydroxide dissolved in 20 parts of water was added to the vessel at a rate such that the pH remained between 7 and 8. As the base was being added, the contents of the vessel were slowly heated to 100° C.

After the base addition was completed, the reaction mixture was heated at reflux (100°-101° C) for three hours. Water was then stripped off under reduced pressure. The residue in the vessel was, then, treated with methanol to remove sodium chloride. The methanol solution was then evaporated to yield 52.7 parts of a viscous oil product identified as 2,4,6-tris[3-dimethylamino-N-(2-hydroxyethyl)propylamino]-s-triazine.

EXAMPLE IV

Into a reaction vessel, equipped as described in Example III, was charged 50 parts of water which was cooled to 0° C. To the cooled water was added 100 parts (0.05 mole) of cyanuric chloride, portionwise. While maintaining the temperature at 0° C, 20.3 parts (0.11 mole) of bis(3-dimethylaminopropyl)amine was added dropwise, with stirring, to the aqueous solution over a period of 1.25 hours.

After the addition was completed, the cooling bath was removed and replaced with heating means. Then the temperature in the vessel was gradually raised to 40° C. Nine and one-tenth parts (0.11 mole) of solid sodium bicarbonate was added to the vessel portionwise over a one-half hour period. The contents of the vessel was then heated at 45° C for 2 hours. A charge of 4.1 parts (0.051 mole) of N-methyl-2-hydroxyethylamine was then added to the vessel. This was followed by the portionwise addition of 4.6 parts (0.051 mole) of solid sodium carbonate over a ten minute period. With stirring the reactants were heated at the reflux temperature, 103° C, for 3 hours. Water was then stripped off under reduced pressure and the residue was extracted with methanol to remove sodium chloride.

The methanol was then evaporated to yield 26.3 parts of an oil identified as 2,4-bis[bis(3-dimethylaminopropyl)amino]-6-(N-methyl-2-hydroxyethylamino)-s-triazine.

EXAMPLE V

Into a reaction vessel equipped with a reflux condenser, thermometer, heating means and a mechanical stirrer was charged 50 parts of xylene, 5 parts (0.06 mole) of solid sodium bicarbonate, 8.7 parts (0.06 mole) of 3-dimethylamino-N-(2-hydroxyethyl)propylamine and 20 parts (0.05 mole) of 2-chloro-4,6-bis(dibutylamino)-s-triazine, the triazine being a cyanuric chloride derivative prepared from 1 mole of cyanuric chloride and 2 moles of dibutylamine.

The reaction mixture was heated, with stirring, at 120° C for 4 hours. Then, the mixture was filtered hot to remove the inorganic material. Xylene was, then, stripped off under reduced pressure and the liquid product was purified by distillation.

There was, thus, obtained 25.6 parts of a product having a boiling point of 170°–179° C at 0.2 Torr and identified as 2,4-bis(dibutylamino)-6-[3-dimethylamino-N-(2-hydroxyethyl) propylamino]-s-triazine.

EXAMPLE VI

Into a reaction vessel, equipped as described in Example III, was charged 150 parts of water which was cooled to 0° C. To the cooled water was added, with stirring, 37 parts (0.2 mole) of cyanuric chloride. With continued stirring and at 0° C, 52 parts (0.4 mole) of N-methyl-2-diethylaminoethylamine was added thereto over a period of 1.25 hours.

After the addition was completed, the cooling bath was removed and replaced with heating means. The contents in the vessel was then heated to 45° C. Contemporaneously with the heating, 34.4 parts (0.41 mole) of solid sodium bicarbonate was added to the vessel over a 25 minute period. The contents was heated at 45° C for another hour. The temperature in the vessel was then raised to 100° C. With the temperature at 100° C, 34.4. parts (0.41 mole) of N-methyl-2-hydroxyethylamine was added to the vessel dropwise followed by the dropwise addition of 8 parts (0.2 mole) of sodium hydroxide, as a 50% aqueous solution, over a ten minute period.

The contents in the vessel was, then, heated at the reflux temperature, 105° C, for 2 hours. While still hot, the contents in the vessel was transferred to a separatory funnel and the organic layer was separated and stripped to yield 69.5 parts (85%) of 2,4-bis(N-methyl-2-diethylaminoethylamino)-6-(N-methyl-2-hydroxyethylamino)-s-triazine. The triazine was purified by distillation, and had a boiling point of 224° C at 0.4 Torr.

The following example illustrates the utility of the instant compounds.

EXAMPLE VII

Utilizing the triazines of Examples III–VI hereof, a series of cellular and resinous products characterized by carbodiimide linkages, as defined in the above-referred to patents, were prepared by the following procedure:

One hundred parts of toluene diisocyanate was admixed with a catalyst in accordance herewith. With stirring, the admixture was heated to its reaction initiation temperature at which time the reactants were transferred to a separate container for foaming.

Table I, below, shows the nature of the resultant products produced hereby:

TABLE I

| Sample | Triazine Type | Amt. | Initiation Temperature, ° C | Max. Exo- ° C | Nature Product | Peaks |
|---|---|---|---|---|---|---|
| A | Ex.III | 2.0 | 95 | 180 | Foam | C-I[3] |
| B | Ex.IV | 2.0 | 100 | 188 | Foam | C-I |
| C | Ex.V | 1.0 | 95 | 197 | Resin | C-I |
| D | Ex.VI | 1.0 | 94 | 140 | Resin | I |
| Control[1] | DMT[2] | 1.0 | 124 | 185 | Foam | C-I |

[1]A control foam utilizing a known carbodiimide catalyst
[2]2,4-bis(diethylamino)-6-N-methylethanolamino-s-triazine, a known carbodiimide catalyst
[3]C carbodiimide peaks I isocyanurate peaks To test the efficacy of the instant catalysts, samples analogous to samples C, D and Control were prepared, but wherein one part of methanol was introduced into the catalyst blend. The results of this procedure are shown in Table II.

TABLE II

| Sample | Initiation Temp.,° C | Maximum Exotherm,° C | Nature of Product | IR Peaks |
|---|---|---|---|---|
| C' | 25 | — | Foam | C-I |
| D' | 25 | 177 | Foam | C-I |
| Control' | 25 | — | No Foam | |

Thus, the unexpected result attendant the conjoint use of an alkanol with the instant triazines becomes evident.

EXAMPLE VIII

Following the procedure of Example VII, a series of rigid cellular products characterized by carbodiimide linkages were prepared from varying organic polyisocyanates, two different catalyst blends and 15 parts of 1,1,2-trichloro-1,2,2-trifluoroethane blowing agent were utilized.

The first catalyst blend, Blend A, comprised a 2:1:1.5:0.5 weight ratio blend of 2,4-bis(diethylamino)-6-N-methylethanolamino-s-triazine; 1,3,5-tris(3-dimethylaminopropyl)-s-hexahydrotriazine; tris(2-chloroethyl)phosphate, and the polysiloxane surfactant. Blend B was the same as Blend A, but utilizing the triazine of Example IV in lieu of the known carbodiimide catalyst.

The following table, Table III, sets forth the ingredients and amounts thereof used to prepare the products, as well as observed physical properties.

TABLE III

| Sample | Isocyanate, Amt. TDI[(1)] | CMDI[(2)] | Catalyst Blend Type | Amt. | Cream Time Sec. | Rise Time Sec. | Max.[(3)] Temp C. | Vol. QT | IR Peaks |
|---|---|---|---|---|---|---|---|---|---|
| 1 | 0 | 100 | A | 10 | 197 | 340 | 111 | 2.0 | C-I Foam |
| 2 | 0 | 100 | B | 8 | 188 | 315 | 118 | 1.3 | — |
| 3 | 10 | 90 | A | 10 | 145 | 265 | 123 | 1.8 | — |
| 4 | 10 | 90 | B | 8 | 145 | 250 | 130 | 1.2 | C-I Foam |

[(1)]an 80:20 weight mixture of 2,4- and 2,6-toluene diisocyanate
[(2)]crude methylene diphenyldiisocyanate
[(3)]reaction initiated at 25° C

We claim:
1. A process for the preparation of a rigid cellular product characterized by carbodiimide linkages comprising:
catalytically condensing an organic polyisocyanate in the presence of a catalytically sufficient amount of a triazine corresponding to the formula:

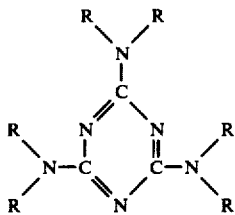

wherein R is either alkyl having from one to six carbn atoms, 2-hydroxyalkyl having from two to six carbon atoms in the alkyl portion, or $(R')_2N$—$R''$ wherein $R'$ is alkyl from one to six carbon atoms and $R''$ is alkylene having from two to ten carbon atoms, and further wherein at least one R must be 2-hydroxyalkyl and at least one R must be $(R')_2N$—$R''$.

2. The process of claim 1 wherein the triazine is selected from the group consisting of 2,4,6-tris[3-dimethylamino-N-(2-hydroxyethyl)propylamino]-s-triazine; 2,4bis[bis(3-dimethyl aminopropyl)amino]-6-(N-methyl-2hydroxy ethyl amino)-2,4-bis(dibutylamino)-6-[3-dimethylamino-N-(2-hydroxyethyl)propylamino]-s-triazine; and 2,4-bis(N-methyl-2-diethylaminoethylamino)-6-(N-methyl-2-hydroxyethylamino)-s-triazine.

3. The process of claim 1 wherein the triazine is used conjointly with an alkanol.

4. The process of the claim 1 wherein the triazine is employed in an amount ranging from about one-half part to about ten parts, by weight, thereof per one hundred parts, by weight, of organic polyisocyanate.

5. The process of claim 1 wherein the organic polyisocyanate is selected from the group consisting of toluene diisocyanate, crude methylene diphenyldiisocyanate and mixtures thereof.

6. The process of claim 1 wherein the triazine is used conjointly with an alkanol and an isocyanate trimerization catalyst.

7. A process for the preparation of a carbodiimide-isocyanurate resin, comprising:
catalytically condensing an organic polyisocyanate in the presence of a catalytically sufficient amount of a triazine corresponding to the formula:

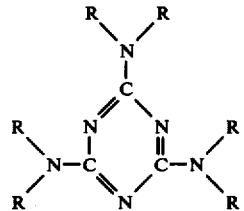

wherein R is either alkyl having from one to six carbon atoms, 2-hydroxyalkyl having from two to six carbon atoms in the alkyl portion , or $(R')_2N'$—$R''$ wherein $R'$ is alkyl from one to six carbon atoms and $R''$ is alkylene having from two to ten carbon atoms and further wherein at least one R must be 2-hydroxyalkyl and at least one R must be $(R')_2N$—$R''$.

* * * * *